(12) United States Patent
Bogert

(10) Patent No.: US 10,092,425 B2
(45) Date of Patent: *Oct. 9, 2018

(54) FLEXIBLE STENT WITH HINGED CONNECTORS

(71) Applicant: C. R. Bard, Inc., Murray Hill, NJ (US)

(72) Inventor: David L. Bogert, Labelle, FL (US)

(73) Assignee: C. R. Bard, Inc., Murray Hill, NJ (US)

(*) Notice: Subject to any disclaimer, the term of this patent is extended or adjusted under 35 U.S.C. 154(b) by 850 days.

This patent is subject to a terminal disclaimer.

(21) Appl. No.: 14/577,753

(22) Filed: Dec. 19, 2014

(65) Prior Publication Data

US 2015/0101748 A1  Apr. 16, 2015

Related U.S. Application Data

(62) Division of application No. 12/666,108, filed as application No. PCT/US2008/067621 on Jun. 20, 2008, now Pat. No. 8,926,689.

(60) Provisional application No. 60/936,917, filed on Jun. 22, 2007.

(51) Int. Cl.
| A61F 2/915 | (2013.01) |
| A61F 2/86 | (2013.01) |
| A61F 2/91 | (2013.01) |
| A61L 31/14 | (2006.01) |
| A61F 2/89 | (2013.01) |
| A61F 2/82 | (2013.01) |
| A61F 2/88 | (2006.01) |

(52) U.S. Cl.
CPC .............. *A61F 2/86* (2013.01); *A61F 2/89* (2013.01); *A61F 2/91* (2013.01); *A61F 2/915* (2013.01); *A61L 31/14* (2013.01); *A61F 2/88* (2013.01); *A61F 2002/828* (2013.01); *A61F 2002/91558* (2013.01); *A61F 2220/0091* (2013.01); *A61F 2250/0071* (2013.01); *Y10T 29/49* (2015.01)

(58) Field of Classification Search
CPC ............... A61F 2/86; A61F 2/91; A61F 2/915
See application file for complete search history.

(56) References Cited

U.S. PATENT DOCUMENTS

| 5,104,404 A | 4/1992 | Wolff |
| 5,507,771 A | 4/1996 | Gianturco |
| 5,556,414 A | 9/1996 | Turi |

(Continued)

FOREIGN PATENT DOCUMENTS

| WO | 199704721 | 2/1997 |
| WO | 2002032347 | 4/2002 |

(Continued)

OTHER PUBLICATIONS

EP 08780878.8 filed Jan. 12, 2010 Extended European Seach Report dated Dec. 6, 2012.

(Continued)

*Primary Examiner* — Jeffry H Aftergut
(74) *Attorney, Agent, or Firm* — Rutan & Tucker, LLP

(57) ABSTRACT

A composite implantable prosthesis including a scaffold with a plurality of axially spaced apart sections connected by one or more bridges, each bridge including one or more hinges, and methods of making the prosthesis. The material of the bridges may be generally distinct from the material of the scaffold.

20 Claims, 4 Drawing Sheets

(56) References Cited

U.S. PATENT DOCUMENTS

| | | | |
|---|---|---|---|
| 5,749,880 A * | 5/1998 | Banas | A61F 2/07 606/198 |
| 6,270,524 B1 * | 8/2001 | Kim | A61F 2/91 606/194 |
| 6,409,754 B1 | 6/2002 | Smith et al. | |
| 6,605,110 B2 | 8/2003 | Harrison | |
| 6,673,103 B1 | 1/2004 | Golds et al. | |
| 6,875,228 B2 | 4/2005 | Pinchasik et al. | |
| 6,911,041 B1 | 6/2005 | Zscheeg | |
| 6,923,829 B2 | 8/2005 | Boyle et al. | |
| 6,942,689 B2 | 9/2005 | Majercak | |
| 7,179,289 B2 | 2/2007 | Shanley | |
| 7,279,004 B2 | 10/2007 | Shanley | |
| 7,323,008 B2 | 1/2008 | Kantor et al. | |
| 7,429,268 B2 | 9/2008 | Shanley et al. | |
| 7,625,398 B2 * | 12/2009 | Clifford | A61F 2/91 623/1.15 |
| 7,819,912 B2 | 10/2010 | Shanley | |
| 7,828,836 B2 | 11/2010 | Besselink | |
| 8,926,689 B2 * | 1/2015 | Bogert | A61F 2/91 623/1.15 |
| 2002/0133222 A1 | 9/2002 | Das | |
| 2002/0198593 A1 | 12/2002 | Gomez et al. | |
| 2003/0009214 A1 | 1/2003 | Shanley | |
| 2003/0014101 A1 | 1/2003 | Harrison | |
| 2003/0191524 A1 | 10/2003 | Hong et al. | |
| 2004/0172127 A1 * | 9/2004 | Kantor | A61F 2/90 623/1.16 |
| 2004/0243216 A1 * | 12/2004 | Gregorich | A61F 2/91 623/1.15 |
| 2005/0038497 A1 * | 2/2005 | Neuendorf | A61F 2/91 623/1.15 |
| 2005/0085894 A1 | 4/2005 | Kershner | |
| 2005/0288771 A1 | 12/2005 | Majercak et al. | |
| 2006/0195175 A1 | 8/2006 | Bregulla | |
| 2006/0266474 A1 | 11/2006 | Burnside et al. | |
| 2008/0051873 A1 | 2/2008 | Cottone et al. | |

FOREIGN PATENT DOCUMENTS

| | | |
|---|---|---|
| WO | 2004064911 A1 | 8/2004 |
| WO | 2005067816 A1 | 7/2005 |
| WO | 2006127126 A1 | 11/2006 |
| WO | 2007005800 A1 | 1/2007 |
| WO | 2009002820 A2 | 12/2008 |

OTHER PUBLICATIONS

PCT/US2008/067621 filed Jun. 20, 2008 International Preliminary Report on Patentability dated Dec. 22, 2009.

PCT/US2008/067621 filed Jun. 20, 2008 International Search Report dated Dec. 29, 2008.

PCT/US2008/067621 filed Jun. 20, 2008 Written Opinion dated Dec. 29, 2008.

U.S. Appl. No. 12/666,108, filed Dec. 22, 2009 Advisory Action dated Dec. 7, 2012.

U.S. Appl. No. 12/666,108, filed Dec. 22, 2009 Final Office Action dated Aug. 30, 2012.

U.S. Appl. No. 12/666,108, filed Dec. 22, 2009 Final Office Action dated Sep. 26, 2013.

U.S. Appl. No. 12/666,108, filed Dec. 22, 2009 Non-Final Office Action dated Mar. 11, 2014.

U.S. Appl. No. 12/666,108, filed Dec. 22, 2009 Non-Final Office Action dated May 21, 2013.

* cited by examiner

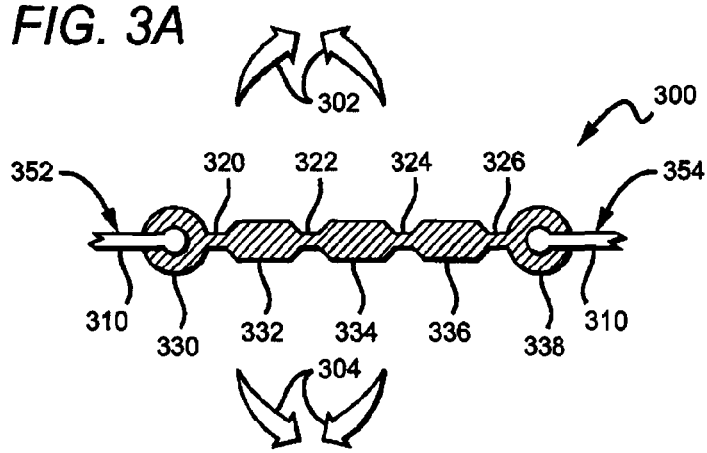
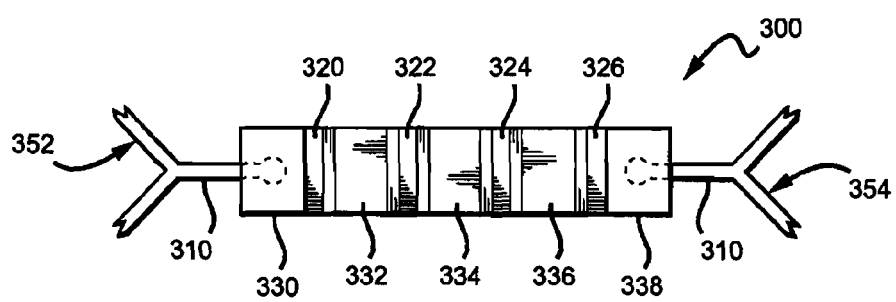
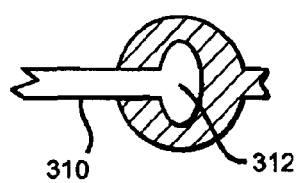 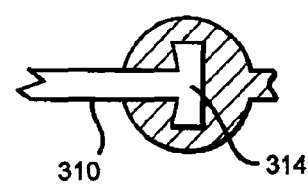
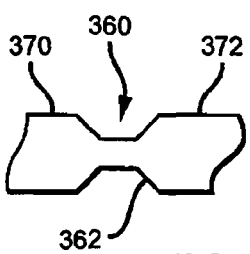 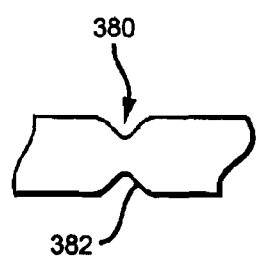

FLEXIBLE STENT WITH HINGED CONNECTORS

PRIORITY

This application is a division of U.S. patent application Ser. No. 12/666,108, now U.S. Pat. No. 8,926,689, filed Dec. 22, 2009, as a U.S. national stage application under 35 USC § 371 of International Application No. PCT/US2008/067621, filed Jun. 20, 2008, claiming priority to U.S. Provisional Application No. 60/936,917, filed Jun. 22, 2007, each of which is incorporated by reference in its entirety into this application.

BACKGROUND

Intraluminal prostheses used to maintain, open, or dilate blood vessels are commonly known as stents. Stent constructions generally include lattice type cylindrical frames that define a plurality of openings. Common frameworks for stents include, for example, individual rings linked along the length of the stent by a linking member, a continuous helically wrapped member (that may include one or more linking members), a braid or a mesh formed into a tubular structure, and a series of interconnected struts. Stents may be formed by arranging one or more members in a pattern along a longitudinal axis to define essentially a cylinder and connecting the one or more members or otherwise affixing them in position (e.g., interconnecting with a filament). Stents may also be formed by cutting openings into a tube of material (e.g., shape memory alloy).

Stents are either self-expanding or balloon expandable. Self-expanding stents are delivered to a blood vessel in a collapsed condition and expand in vivo following the removal of a constraining force and/or in the presence of an elevated temperature (due to material properties thereof), whereas balloon expandable stents are generally crimped onto a balloon catheter for delivery and require the outwardly directed force of a balloon for expansion. Stents can be made of various metals and polymers and can include a combination of self-expanding and balloon expandable properties.

Synthetic vascular grafts are routinely used to restore the blood flow in patients suffering from vascular diseases. For example, prosthetic grafts made from expanded polytetrafluoroethylene (ePTFE) are commonly used and have shown favorable patency rates, meaning that depending on a given time period, the graft maintains an open lumen for the flow of blood therethrough. Grafts of ePTFE may be manufactured in a number of ways, including, for example, extrusion of a tube (seamless), extrusion of a sheet that is subsequently formed into a tube (one or more seams), helical wrapping of ePTFE tape around a mandrel (e.g., multiple seams or preferably a single helical seam), etc. Grafts can also be created from fibers woven or knitted into a generally tubular shape.

It is known in the art to use stents in combination with vascular grafts to form stent-grafts. Because stent-grafts are often intraluminally deployed in vessels of varying sizes and tortuosity, flexibility can be an important consideration. Flexibility can be imparted to a stent-graft in a variety of ways, including, for example, connection of the stent to the one or more graft layers, configuration of the stent and/or graft layer(s), spacing of the stent struts, rings, or members along the length of the graft(s), etc. Another important consideration in the design of a stent-graft is the ability of the stent to withstand stress and fatigue, caused, for example, by plastic deformations occurring at strut junctions when the stent is subjected to circumferential forces. Stent strength can be enhanced through material choice, stent configuration, arrangement and configuration of graft layers, connecting members between stent members, etc. Another consideration in the design of certain stent-grafts is properties to resist kinking of the stent-graft. For example, when a stent-graft is positioned in a bend in a blood vessel or bypass graft, depending on the acuteness of the angle of the bend, the stent-graft can potentially kink and thereby become unsuitable for passage of blood therethrough.

The following references relate to stents and stent-grafts: U.S. Pat. No. 5,104,404 to Wolff; U.S. Pat. No. 5,507,771 to Gianturco; U.S. Pat. No. 5,556,414 to Turi; U.S. Pat. No. 6,409,754 to Smith et al.; U.S. Pat. No. 6,605,110 to Harrison; U.S. Pat. No. 6,673,103 to Golds et al.; U.S. Pat. No. 6,875,228 to Pinchasik et al.; and U.S. Pat. No. 6,911,041 to Zscheeg, each of which is incorporated by reference in its entirety into this application.

It is also known in the art to use outsert plastic injection molding to create long lasting, fatigue resistant hinges. The hinge is created from a thin section of plastic that generally connects two segments of a part to keep them together and permit the two segments to pivot, generally by opening and closing, repeatedly. The integrated hinge is very fatigue resistant because the long polymer molecules of the plastic are aligned across the hinge. Typically, such hinges are used in containers such as toolboxes, fish tackle boxes, and other high volume applications.

Generally, the hinge is created from very flexible plastic materials such as polypropylene or polyethylene. The material is chosen to permit repeated cycles of the hinge without failing. Different techniques can be used to orient the fibers across the hinge to increase the hinge strength. When molding the part, the hinge may be oriented, relative to the injection flow, so that the plastic flows across the hinge. In addition, when a part comes out of the mold, it may be flexed while it is still hot or warm to ensure that the fibers are correctly oriented. Finally, the hinge could be made by coining, which compresses the hinge to its predetermined thickness after the part has been injection molded. The strain induced is greater than the yield stress of the plastic, which plastically deforms the hinge. However, the amount of coining should be less than the ultimate stress, to keep the hinge from fracturing.

The following references relate to injection molded hinges: U.S. Pat. No. 4,518,092 to Contreras, Sr; U.S. Pat. No. 5,353,948 to Lanoue et al.; and U.S. Pat. No. 5,762,852 to Hettinga, each of which is incorporated by reference in its entirety into this application.

Applicants have recognized that it would be desirable to provide a stent or stent-graft that is axially and/or angularly flexible and able to maintain strength under high stress/fatigue environments, embodiments of which are described herein along with methods of making the same.

BRIEF SUMMARY

In one embodiment, a composite implantable prosthesis, includes a scaffold including a plurality of axially spaced apart circumferential sections circumscribing a longitudinal axis from a first end to a second end to define a portion of essentially a cylinder, the scaffold comprising an elastic first material, and one or more bridges connecting adjacent circumferential sections along the longitudinal axis, each bridge including one or more hinges and comprising a flexible second material distinct from the first material.

In one embodiment, a method of making a composite implantable prosthesis includes forming a scaffold including a plurality of axially spaced apart circumferential sections circumscribing a longitudinal axis from a first end to a second end to define a portion of essentially a cylinder, the scaffold comprising an elastic first material, and connecting each circumferential section of the scaffold to an adjacent circumferential section with one or more bridges, each bridge including one or more hinges and comprising a flexible second material distinct from the first material.

In another embodiment, a method of making a composite implantable prosthesis includes forming a generally cylindrical-shaped stent from a first material having sufficient elasticity and radial rigidity to remain open when inserted into a lumen, the stent defining a plurality of circumferential sections, and connecting adjacent circumferential sections of the stent using one or more hinged connectors formed from a second material having sufficient flexibility to conform the stent to contours in the lumen.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 3A is a cross-sectional view of one embodiment of a bridge connecting circumferential sections.

FIG. 3B is a view of the bridge of FIG. 3A rotated approximately 90 degrees.

FIG. 3C is an enlarged view of one embodiment of the connection between a bridge and a circumferential section.

FIG. 3D is an enlarged view of another embodiment of the connection between a bridge and a circumferential section.

FIG. 3E is an enlarged view of one embodiment of a hinge connecting bridge sections of FIG. 3A.

FIG. 3F is an enlarged view of another embodiment of a hinge connecting bridge sections.

DESCRIPTION OF THE PREFERRED EMBODIMENTS

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "body," "patient," "host" and "subject" refer to any human or animal subject and are not intended to limit the systems or methods to human use, although use of the subject invention in a human patient represents a preferred embodiment.

Figure 1:
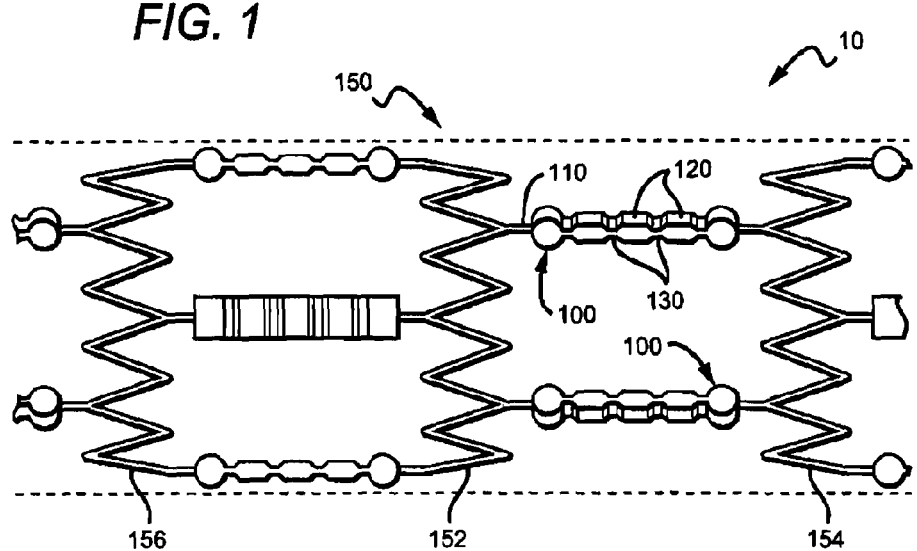
FIG. 1 is a partial side view of one embodiment of an implantable prosthesis including a scaffold with circumferential sections and bridges with hinges.

Referring now to FIG. 1, a portion of a composite implantable prosthesis 10 is shown, which includes a scaffold 150 with a plurality of circumferential sections 152, 154 and 156, connected by bridges 100 including hinges 130. The scaffold 150 provides radial strength to open a narrowed section of a lumen and maintain that section in an open position to permit blood flow therethrough. In the embodiment shown, the scaffold 150 includes a plurality of spaced apart circumferential sections that circumscribe a longitudinal axis from a first end of the prosthesis to a second end thereof to define a portion of essentially a cylinder. The circumferential sections 152, 154, and 156 of prothesis 10 shown in FIG. 1 are connected together via bridges 100, which provide axial and angular flexibility, as well as prolonged fatigue life to the prothesis 10 so that the prothesis is able to conform to the body lumen in which it is deployed. Each circumferential section 152, 154, and 156 may include one or more protrusions 110 that provide a connection point between the circumferential section and the bridge 100. The bridges 100 include hinges that permit the bridge to flex. In this embodiment, the bridges 100 include four hinges 130, but other embodiments may have bridges with one, two, three, four or more hinges 130. Also, while the bridges shown in FIG. 1 have the same number of hinges, in other embodiments, the number of hinges 130 may vary for each bridge along the length of the scaffold 150. For example, the bridges positioned near the ends of the scaffold may include four or less hinges, while the bridges positioned near the middle of the scaffold may include four or more hinges, as discussed in more detail below.

The circumferential sections may be discrete individual stent members or spaced apart portions of a continuous stent member that together permit the scaffold to collapse or expand radially in a uniform or non-uniform fashion. The circumferential sections may be formed by standard stent designs, such as, for example, segmented stents, helical stents, solid stents, or combinations thereof. In addition, the circumferential sections may have self-expanding or balloon-inflatable properties, or combinations thereof.

FIG. 1 shows the circumferential sections 152, 154, 156 as distinct, individual annular members aligned along the longitudinal axis of the scaffold 150. Each section is configured in an undulating form made of peaks and troughs. The circumferential sections are aligned so that the trough of one circumferential section 152 may be aligned with a peak of the adjacent circumferential section 154. The bridge 100 may connect adjacent circumferential sections at the trough of the first circumferential section 152 and the peak of the adjacent section 154. The adjacent circumferential sections 152 and 154 are spaced a sufficient distance apart to prevent interference between the adjacent sections upon radial compression or tortuous bending of the scaffold 150.

Many other circumferential section configurations are also possible and within the scope of the invention, such as, for example, sinusoidal patterns, meandering curve patterns, other zigzag patterns, or other curvilinear patterns. Any type of pattern or shape can be combined with other patterns or shapes to form non-uniform circumferential sections. Moreover, it should be appreciated that the shape, size, thickness, material and/or other characteristic of the circumferential sections can be varied along the length of the scaffold. Therefore, each circumferential section 152, 154, and 156 need not be of the same material, shape, size, or configuration. Further, the undulations are not limited to zig-zag patterns but can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern.

The circumferential sections are sufficiently elastic and radially rigid to remain open when inserted into a body lumen. Additionally, the circumferential sections may be designed to expand and collapse to aid in the delivery of the prosthesis within the body. Therefore, the sections may be formed of a shape memory material, including, for example, shape memory metals, shape memory alloys, super elastic shape memory metal alloys, linear elastic shape memory alloy, metal alloys, shape memory polymers, polymers, bio-resorbable material, and combinations thereof. One preferred shape memory material is Nitinol, while another is a cobalt chrome alloy. The sections may also be formed of metal, such as, for example, stainless steel, platinum, and Elgiloy, or certain polymers.

As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the prosthesis described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes.

As shown in FIG. 1, the bridges 100 connect longitudinally adjacent circumferential sections 152 and 154. The bridges are sufficiently flexible to allow the prosthesis to conform to lumen contours, and in one embodiment are formed from a separate material than the circumferential sections 152, 154, 156. In one embodiment, the bridges are formed from a plastic material, such as, for example, polyurethane, polyethylene, polypropylene, bioabsorbable polymer, or combinations thereof. The bridges 100 connecting adjacent sections 152 and 154 may be spaced at any interval around the scaffold, but in one embodiment are spaced at essentially equal distances around the circumferential section. The adjacent circumferential sections may also be connected by any number of bridges, but preferably are joined by one to five bridges. The bridges 100 are disposed generally parallel to the longitudinal axis of the scaffold 150, but different orientations of the bridge with respect to the longitudinal axis of the scaffold 150 are also envisioned to fall within the scope of the invention. For example, a bridge may be diagonally offset from the longitudinal axis of the scaffold such that a longitudinal axis of the bridge forms an acute angle with the longitudinal axis of the scaffold. Also, a bridge may be disposed generally circumferentially with respect to the longitudinal axis of the scaffold, such that, for example, each bridge section of the bridge is attached to two adjacent circumferential sections.

A bridge may contain any number of hinges which may be arranged linearly along the length of the bridge and the number of hinges may vary for different bridges of the scaffold. In the embodiment of FIG. 1, the bridges include four hinges 130, integrally formed, connecting five bridge sections 120. The hinges 130 generally have a smaller thickness than other portions of the bridge to permit the hinge to pivot at the hinge location. The hinges 130 may pivot around an axis tangential to the scaffold 150 circumference. Preferably, a single bridge will possess one to ten hinges, and more preferably one to three hinges. The bridge may be oriented to permit bending in any direction and need not be aligned as shown. Moreover, each hinge within a single bridge need not be aligned to pivot around parallel axes. For example, one hinge may be aligned as shown in FIG. 1 to permit the bridge to pivot around an axis that is tangential to the circumference of the prosthesis surface, and an adjacent hinge on the same bridge may be oriented ninety degrees therefrom to permit rotation around a perpendicular axis. Further, while bridges 100 are shown with a single row of bridge sections 120, other embodiments may have two, three, or more rows of interconnected bridge sections and hinges.

Figure 2:
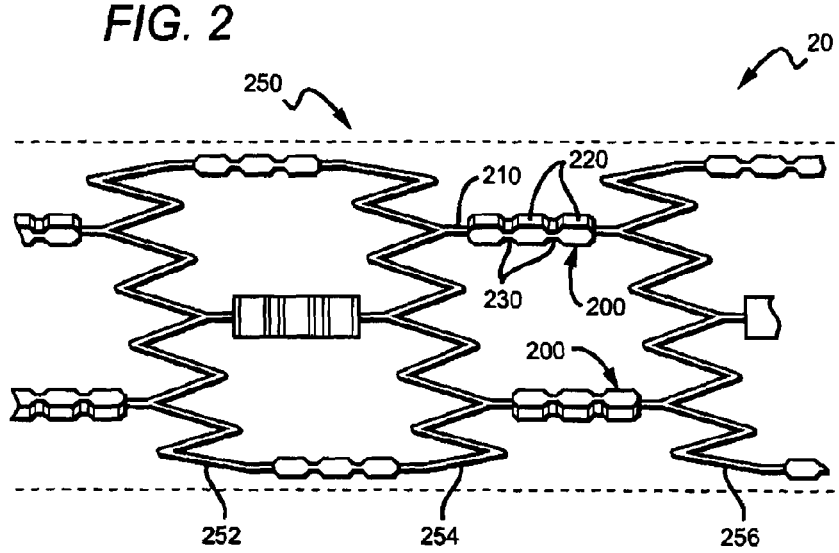
FIG. 2 is a partial side view of another embodiment of an implantable prosthesis including a scaffold with circumferential sections and bridges with hinges.

FIG. 2 illustrates another embodiment of a prosthesis, in which circumferential sections 252, 254, 256 are formed by adjacent windings of one or more elongate members helically disposed along a longitudinal axis of a scaffold 250. As with the circumferential sections of scaffold 150, the distance between adjacent helical windings 252, 254, 256 of the elongate member may be approximately equal, or may vary in a uniform or non-uniform manner along the length of the scaffold 250. For example, the distance between the first two helical windings 252 and 254 may be greater than or less than the distance between helical windings 254 and 256. Moreover, the distance between adjacent helical windings could progressively increase or decrease along the length of the scaffold, or could alternate between different distances. For embodiments including two or more elongate members, the members could be helically wound in different directions and/or with different helical angles. In prosthesis 20, the bridges 200 of scaffold 250 connect adjacent turns of a single helically wound elongate member, and thus, each section 252, 254, 256 comprises a subsequent helical turn of the elongate member. Alternatively, one or more circumferential sections may include two or more turns of the helical member (e.g., with minimal space between turns), the two or more turns being connected via a polymer graft and/or substrate or by other means known to one skilled in the art.

As shown in FIG. 2, adjacent sections, such as 254 and 256, are connected by bridges 200 spaced circumferentially from one another. In a preferred embodiment, adjacent sections are connected by four bridges, but other embodiments are also possible, as discussed above in connection with FIG. 1. Similarly, although each bridge 200 shown in FIG. 2 includes two hinges, any number of hinges could be used for the bridges and the number of hinges may vary from bridge to bridge as discussed above. The hinges of the bridge connect bridge sections along the length of the bridge, and the shape of the bridge sections may vary along the length of the bridge. For example, the bridge sections connected to the scaffold may be spherical, while bridge sections therebetween may be cylindrical. Further, the cross-sectional shape of a bridge section may vary along its length according to the shape of the outer surface of the bridge section (e.g., frusto-conical, followed by circular, followed by frusto-conical, etc.), as explained in more detail below.

Referring now to FIG. 3A, an enlarged cross-sectional view of one embodiment of a flexible bridge 300 is shown connecting adjacent circumferential sections of the scaffold, the bridge sections 330, 338 at the ends of the bridge 300 being formed over a protrusion 310 extending from each of the adjacent circumferential sections. The bridge 300 in this embodiment includes four hinges 320, 322, 324, 326, but other embodiments may include fewer hinges or more hinges, as discussed above. The hinges 320, 322, 324, 326 are shown connecting adjacent bridge sections 330, 332, 334, 336, 338 to one another. The protrusion 310 in this embodiment provides a location on the circumferential section to which the bridge can connect. The bridge may be formed over a distal end of the protrusion 310, as shown, or may be formed over a substantial length of the protrusion, including the entire length thereof. Alternatively, or in addition to the formation over a protrusion, the bridge may be formed over any other portion of the circumferential section of the scaffold.

The protrusion 310 may be an extension of the scaffold or may be a separate member connected to the circumferential section thereof. The protrusion may extend from or connect to any part of the circumferential section, but in a preferred embodiment, the protrusion extends from a position on the circumferential section that is relatively closer to an adjacent circumferential section to which it is to connect (e.g., a peak of a circumferential section with a zig-zag configuration). The protrusion may be a linear or non-linear member with a length such that the formation of the bridge over less than an entire length thereof spaces the bridge connection from the circumferential section of the scaffold in order, for example, to prevent potential interference during radial collapse of the prosthesis to its reduced deployed configuration with an outer perimeter smaller than the outer perimeter at an expanded configuration. The protrusion may include a non-uniform profile to increase the connection strength between the bridge and the scaffold. For example, as shown in FIGS. 3A and 3B, the protrusion 310 may include structure, such as an enlargement, at its distal end. FIGS. 3D and 3E illustrate two embodiments of enlarged distal ends for the protrusion 310. In FIG. 3D, the distal end of the protrusion 310 is in the form of a knob 312, while in FIG. 3E, the distal end of the protrusion is shown in the shape of a mallet 314. Alternate shapes or forms are also possible for the enlarged distal end of the protrusion to provide increased surface area over which the bridge can be formed.

The bridges may be attached to the circumferential sections of the scaffold in a variety of ways known to one skilled in the art. For example, the bridges may be attached using an adhesive or a solvent or may be encapsulated between graft layers along with all or a portion of the scaffold. However, in a preferred embodiment, the bridge is molded (e.g., outsert injection molded) over a portion of the scaffold. The bridge may be molded over a portion of protrusions extending from the circumferential sections or alternatively, in scaffold embodiments with or without protrusions, over non-protruding portions thereof (e.g., a peak of a circumferential section). The hinges may be integrated into the bridge during the formation thereof (e.g., during a molding process), or may be separately attached to bridge sections to form the bridge. In a preferred embodiment, the hinges are formed along with the bridge sections (e.g., by outsert injection molding) in order, for example, to reduce the necessary processing steps required to form the bridge.

In one embodiment, a polymer is injection molded over a portion of the circumferential sections of the scaffold, such as protrusions 310, such that the long polymer chains forming the hinges are oriented in the direction that the hinges are designed to flex. In a preferred embodiment, the long polymer chains forming the hinges are oriented generally parallel to the longitudinal axis of the bridge. To improve the connection between the bridge and the circumferential sections of the scaffold, various techniques known to one skilled in the art can be utilized. For example, if the bridge is formed of polyethylene, the mold can be heated to between about 50 degrees C. and about 70 degrees C. to improve the flow of the polyethylene around the scaffold sections. Various techniques know to one skilled in the art can also be used to improve the hinging properties of the bridge. Again, with respect to the example of a polyethylene bridge, after the mold is heated to between about 50 degrees C. and about 70 degrees C., the prosthesis is removed from the mold and the hinges are immediately flexed two or more times prior to the setting of the polymer. In another embodiment, the hinges are created by a coining process as known by one skilled in the art, which includes compressing the bridge at spaced apart sections to form the hinge.

The hinge may be oriented in any direction and different hinges in the same bridge may be oriented in the same direction or different directions. The orientation of the hinge, as used herein, refers to the direction in which the bridge is permitted to flex based upon, for example, the reduced thickness of the bridge along a length of a surface of the bridge. Thus, for example, in embodiments in which the bridge has a multisided geometric shape in cross-section, such as a triangle, rectangle, square, etc., the orientation of the hinge is defined by the reduced wall thickness of the bridge along one or more of the sides. When more than one side of the bridge has a reduced cross-section along the same length (e.g., on opposite sides), a hinge is formed that permits the bridge to flex in more than one direction. Similarly, in embodiments in which the bridge has a curved outer surface, such as a circle, oval, etc., the reduced thickness of the bridge can come at one or more different circumferential positions along the same length of the bridge surface to define hinge orientation(s).

Referring again to FIG. 3A, the hinges 320, 322, 324, 326 are formed by a reduced wall thickness of the bridge 300 in a first side and a second side opposite the first side. FIG. 3B is a view of the bridge from a direction turned approximately 90 degrees from the view of FIG. 3A, showing the hinge width spanning the entire thickness of the bridge wall along a direction generally perpendicular to the longitudinal axis of the bridge. Thus, the orientation of the hinges 320, 322, 324, 326 in the embodiment shown in FIGS. 3A-3B is in the direction indicated by arrows 302 and 304, as it is in those directions that the hinges are permitted to flex. The orientation of the hinges can be tailored such that the bridges have the ability to flex in several different directions, increasing the overall flexibility of the stent and thereby improving the fatigue resistance thereof.

An enlarged view of a hinge is shown in FIG. 3E and FIG. 3F to illustrate examples of potential configurations thereof. In certain embodiments, such as embodiments in which the hinges are integrally formed through an injection molding process, the reduced wall thickness of the bridge that forms the hinge imparts a particular shape to the portion of the bridge section to which it is attached. For example, FIG. 3E shows a hinge 360 that is formed between bridge sections 370 and 372 such that the sides 362 of the bridge sections 370, 372 attached to the hinge 360 form an oblique angle with respect to the longitudinal axis of the bridge, imparting a particular shape to the bridge section along the length of the sides 362. In other embodiments, such as that shown in FIG. 3F, the sides 382 of the bridge sections define a curved configuration with the hinge 380. It should be appreciated that the sides of the bridge sections attached to the hinge need not be uniform and, indeed, each side may have a different disposition and/or configuration. Moreover, in embodiments in which opposing sides of the bridge have reduced thicknesses (e.g., recesses), the recesses may be uniform or non-uniform with respect to the distance from the outer perimeter of the bridge.

Figure 4A:
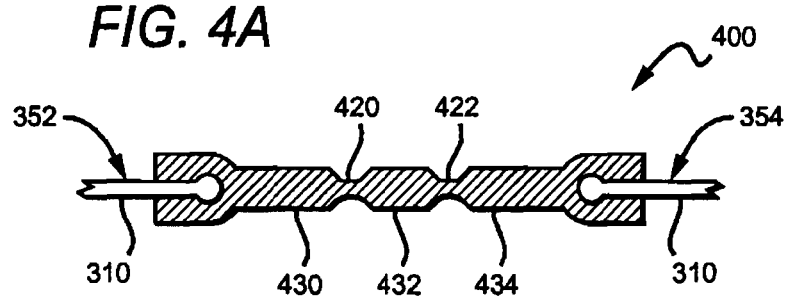
FIG. 4A is a cross-sectional view of another embodiment of a bridge connecting circumferential sections.
Figure 4B:
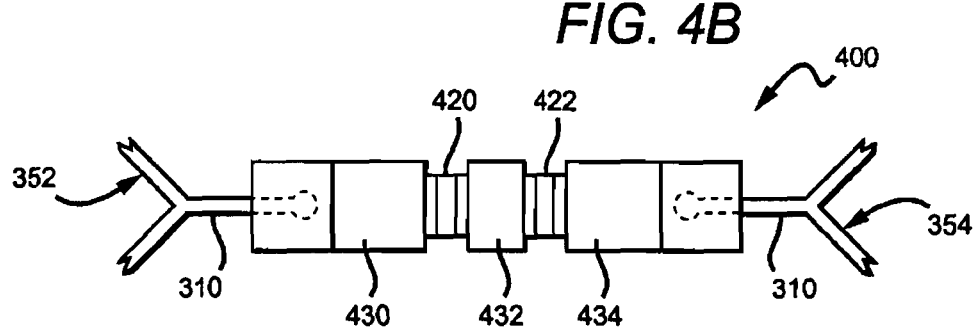
FIG. 4B is a view of the bridge of FIG. 4A rotated approximately 90 degrees.
Figure 4C:
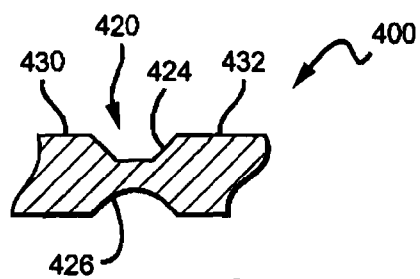
FIG. 4C is an enlarged view of one embodiment of a hinge connecting bridge sections of FIG. 4A.

FIGS. 4A-4B illustrate a bridge 400 with a generally cylindrical shape, in which the bridge sections 430, 434 at the ends of the bridge 400 are longer than those shown in FIGS. 3A-3B, covering a more substantial length of the protrusion 310. Also, as seen in FIG. 4B, the hinge width along the thickness of the bridge wall when viewed from the same direction as depicted in FIG. 3B is reduced and thus, hinges 420, 422 is formed by a reduction in all sides (i.e., the entire circumference) of the bridge 400. FIG. 4C is an enlarged cross-sectional view of the hinge 420 showing a reduced wall thicknesses of different configurations from different sides of the bridge 400. On a first side of the bridge 400, the sides 424 of the bridge sections 430, 432 attached to the hinge 420 form an oblique angle with respect to the longitudinal axis of the bridge, while on the second side of the bridge 400 opposite the first side, the sides 426 of the bridge sections 430, 432 form a curve (arch) with the hinge 420.

Figure 6:
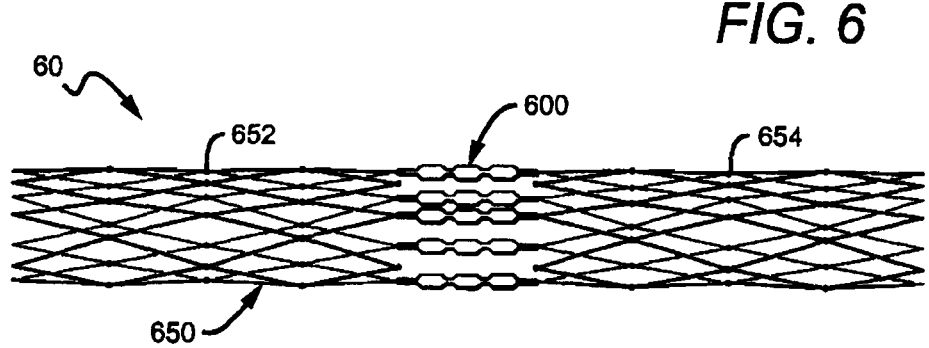
FIG. 6 is a partial side view of another embodiment of an implantable prosthesis including a scaffold with circumferential sections and bridges with hinges.
Figure 5:
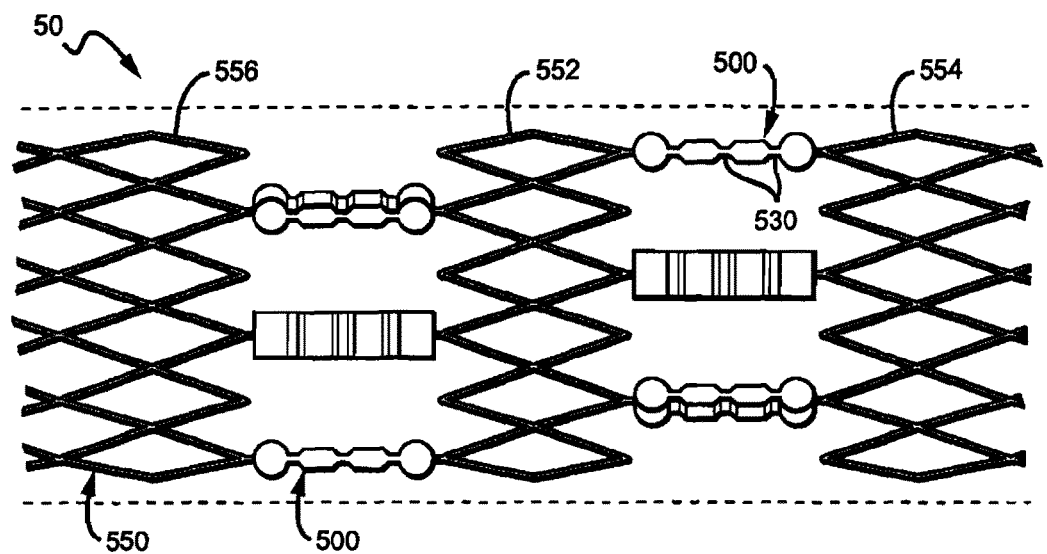
FIG. 5 is a partial side view of one embodiment of an implantable prosthesis including a scaffold with circumferential sections and bridges with hinges.
Figure 7:
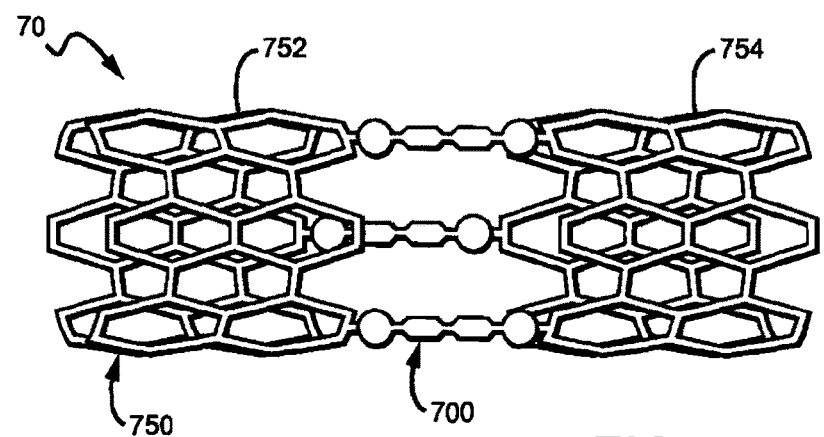
FIG. 7 is a partial side view of another embodiment of the implantable prosthesis including a scaffold with circumferential sections and bridges with hinges.

FIGS. 5-7 depict embodiments of a prothesis, as described herein, with different types of scaffolds, including circumferential sections, and bridges, including hinges. FIG. 5 is a partial side view of a prosthesis 50, showing three circumferential sections 552, 554, 556 of a scaffold 550 connected by bridges 500. Adjacent circumferential sections of scaffold 550 are connected by six bridges 500 circumferentially spaced apart and each bridge 500 contains three hinges 530. Circumferential section 552 is shown with a single closed cell configuration, while circumferential sections 554 and 556 are shown with dual closed cell configurations. The closed cell lattice is composed of connected struts, which may be straight, as shown, or in a curved configuration to form closed cells of various different shapes. Preferably, the circumferential sections are made of Nitinol, and more specifically, are laser cut from a Nitinol tube. For example, in one embodiment, longitudinal slits are laser cut into a solid Nitinol tubular section in such a manner as to form the desired closed cell configuration upon expanding the tube. It should be appreciated that other methods of forming the circumferential sections are possible and are within the scope of the invention. For example, the zigzag strut configuration previously described may be joined or connected together to form the single or plural closed cell lattice. The scaffold may be any stent structure suitable for inserting into a body lumen to hold open that lumen to permit fluid flow, including discrete annular members and elongate members helically wrapped to form the scaffold structure.

FIG. 6 depicts a radially compressible/expandable wire cage scaffold 650 of prosthesis 60, the scaffold 650 including circumferential sections 652 and 654 connected by bridges 600. FIG. 7 depicts a scaffold 750 of prosthesis 70, the scaffold 750 including circumferential sections 752 and 754 connected by bridges 700. As mentioned, the scaffold/circumferential sections may be any stent structure, such as, for example, those shown and described in U.S. Pat. No. 4,886,062 to Wiktor, U.S. Pat. No. 5,104,404 to Wolff, U.S. Pat. No. 5,133,732 to Wiktor, U.S. Pat. No. 5,507,771 to Gianturco, U.S. Pat. No. 5,556,414 to Turi, and U.S. Patent Application Publication No. 2005/0228480 to Douglas et al., each of which are incorporated by reference in their entirety into this application. It should be appreciated that any shape, size, thickness, material or other characteristic of the circumferential section can be varied along the length of the implantable prosthesis. Moreover, any combination of different circumferential sections may be used together to vary each section along the length of the implantable prosthesis.

The examples discussed herein may include a graft or substrate layer. This layer in one embodiment is a generally tubular polymer member, which is indicated by the dotted line in the drawings. The polymer member may be disposed along the inner surface, the outer surface, or both surfaces of the scaffold. The polymer member may cover all or part of the scaffold, including the bridges. For example, the polymer member may extend the entire length of the scaffold. In some embodiments, the polymer member may include several circumferential members spaced apart along the longitudinal axis of the scaffold. If the prosthesis includes both an inner and outer graft or substrate layer, the two layers may be connected together through the openings of the scaffold, such as by bonding. Potential materials for a graft or substrate layer include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene fibers, aramid fibers, and combinations thereof. The substrate may be longitudinally compressed before attaching to the scaffold. For example, a substrate may be longitudinally compressed from a first length to a second length, which is approximately 50% to 97% of the first length. Longitudinal compression of a graft or substrate is described in U.S. Pat. No. 4,955,899 to Della Coma et al., which is incorporated by reference in its entirety in this application.

The graft or substrate layer may additionally include a bioactive agent. Bio-active agents can be coated onto a portion of the graft or substrate layer and/or can be disposed along the scaffold for controlled release of the agents once the prosthesis is implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method comprising a step of making an implantable prosthesis by forming a scaffold, the scaffold comprising:
    a plurality of axially spaced-apart circumferential sections defining a cylindrical portion around a longitudinal axis, wherein one or more of the circumferential sections includes a protrusion;
    an elastic first material selected from the group consisting of stainless steel, shape-memory metals, shape-memory alloys, super-elastic shape-memory metal alloys, metal alloys, linear, elastic shape-memory alloys, shape-memory polymers, polymers, bio-resorbable materials, Nitinol, cobalt-chrome alloys, and combinations thereof; and
    one or more polymer bridges, each polymer bridge surrounding a portion of the scaffold, at least one polymer bridge encasing part of the protrusion, the one or more polymer bridges including one or more hinges, wherein each polymer bridge is disposed between two adjacent circumferential sections.

2. The method of claim 1, wherein the one or more hinges are integrally formed in the one or more polymer bridges.

3. The method of claim 2, wherein the plurality of axially spaced-apart circumferential sections are helically disposed around the longitudinal axis.

4. The method of claim 2, wherein the plurality of axially spaced-apart circumferential sections are disposed in circles around the longitudinal axis.

5. The method of claim 2, further comprising disposing a first generally tubular ePTFE member along an inner surface of the scaffold.

6. The method of claim 5, further comprising disposing a second generally tubular ePTFE member along an outer surface of the scaffold.

7. The method of claim 6, further comprising bonding the second generally tubular ePTFE member to the first generally tubular ePTFE member through openings in the scaffold.

8. The method of claim 1, wherein the one or more hinges are disposed linearly along a length of each polymer bridge.

9. The method of claim 1, wherein the one or more hinges comprise long polymer molecules disposed across a width of the one or more hinges.

10. The method of claim 1, wherein the at least one polymer bridge encases a distal end of the protrusion.

11. The method of claim 10, wherein the plurality of axially spaced-apart circumferential sections are disposed in circles around the longitudinal axis.

12. The method of claim 1, wherein the at least one polymer bridge encases most of the protrusion.

13. The method of claim 12, wherein the plurality of axially spaced-apart circumferential sections are helically disposed or disposed in circles around the longitudinal axis.

14. The method of claim 1, wherein the protrusion includes an enlarged distal end and the at least one polymer bridge encases the enlarged distal end.

15. The method of claim 14, wherein the plurality of axially spaced-apart circumferential sections are helically disposed or disposed in circles around the longitudinal axis.

16. The method of claim 1, wherein the one or more hinges are located at reduced-thickness regions of the one or more polymer bridges.

17. The method of claim 1, wherein at least one of the one or more polymer bridges comprises two or more hinges.

18. A method comprising forming an implantable prosthesis scaffold, the scaffold comprising:

a plurality of axially spaced apart circumferential sections including struts joined at vertexes, wherein one or more of the circumferential sections includes a protrusion from one of the vertexes, the circumferential sections comprising an elastic first material; and one or more bridges comprising:
  one or more hinges; and
  a flexible second material different from the elastic first material, wherein each of the one or more bridges connects to one of the vertexes of a circumferential section and to one of the vertexes of an adjacent circumferential section, and wherein at least one bridge of the one or more bridges encases part of the protrusion.

19. A method comprising:

providing a plurality of axially spaced apart, circumferential, implantable-prosthesis sections comprising an elastic first material; and providing one or more bridges comprising one or more hinges and a flexible second material different from the first material, followed by connecting each bridge between two adjacent sections.

20. A method comprising a step of making an implantable prosthesis by forming a scaffold, the scaffold comprising:

a plurality of axially spaced-apart circumferential sections defining a cylindrical portion around a longitudinal axis;

an elastic first material; and one or more bridges comprising a flexible second material different from the elastic first material, the one or more bridges including one or more hinges, at least one of the one or more bridges including two or more hinges, wherein each of the one or more bridges is disposed between two adjacent circumferential sections.

* * * * *